(12) United States Patent
Yoshidome

(10) Patent No.: US 8,918,481 B2
(45) Date of Patent: Dec. 23, 2014

(54) MEDICAL IMAGE DISPLAY SYSTEM AND MEDICAL IMAGE COMMUNICATION METHOD

(75) Inventor: Takumi Yoshidome, Utsunomiya (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 488 days.

(21) Appl. No.: 12/835,374

(22) Filed: Jul. 13, 2010

(65) Prior Publication Data

US 2011/0016306 A1 Jan. 20, 2011

(30) Foreign Application Priority Data

Jul. 15, 2009 (JP) .................................. 2009-166892
Jul. 1, 2010 (JP) .................................. 2010-151085

(51) Int. Cl.
*G06F 15/16* (2006.01)
*G06F 19/00* (2011.01)

(52) U.S. Cl.
CPC .................................. *G06F 19/321* (2013.01)
USPC ........... 709/219; 709/203; 709/206; 709/226; 382/130; 382/128; 382/132; 600/439; 600/407; 600/410

(58) Field of Classification Search
CPC ...... G06F 19/321; G06F 15/16; G06T 7/0038
USPC .......... 709/203, 206, 219, 226; 382/128–132, 382/173; 600/439, 407, 410
See application file for complete search history.

(56) References Cited

U.S. PATENT DOCUMENTS

| 8,150,708 | B2 * | 4/2012 | Kotula et al. ...................... 705/2 |
| 8,194,958 | B2 * | 6/2012 | Moriya ........................... 382/130 |
| 2001/0027272 | A1 * | 10/2001 | Saito et al. ..................... 600/426 |
| 2002/0099273 | A1 * | 7/2002 | Bocionek et al. ............. 600/300 |
| 2003/0097070 | A1 * | 5/2003 | Nakaya et al. ................. 600/447 |
| 2005/0244082 | A1 * | 11/2005 | Yamatake ..................... 382/305 |
| 2005/0251009 | A1 * | 11/2005 | Morita et al. ................. 600/407 |

(Continued)

FOREIGN PATENT DOCUMENTS

| JP | 2004-80612 A | 3/2004 |
| JP | 2006-6449 | 1/2006 |
| JP | 2006-314626 A | 11/2006 |

OTHER PUBLICATIONS

Office Action issued Feb. 18, 2014, in Japanese Patent Application No. 2010-151085 with partial English translation.

(Continued)

*Primary Examiner* — Quang N Nguyen
*Assistant Examiner* — Benjamin M Thieu
(74) *Attorney, Agent, or Firm* — Oblon, Spivak, McClelland, Maier & Neustadt, L.L.P.

(57) ABSTRACT

A medical image display system according to an embodiment including a server that provides medical image display data and display/clinical applications and a terminal device that can access the server by way of a network, the system, configuring the medical image display data so that pieces of image display information of a plurality of types including medical image information and interface information for user operation are arranged in a multilayered manner; transmitting the pieces of image display information of a plurality of types to the terminal device from the server, assigning them to communication protocols of different types; synthetically combining and displaying the pieces of image display information of a plurality of types transmitted from the server with use of the terminal device; and generating operator information by utilizing the interface information for user operation displayed on the terminal device, and transmitting the operator information to the server by way of the network.

14 Claims, 6 Drawing Sheets

(56) References Cited

U.S. PATENT DOCUMENTS

| | | |
|---|---|---|
| 2006/0242143 A1* | 10/2006 | Esham et al. .................. 707/6 |
| 2006/0274885 A1* | 12/2006 | Wang et al. .................. 378/65 |
| 2007/0130165 A1* | 6/2007 | Sjoblom et al. .............. 707/10 |
| 2007/0237369 A1* | 10/2007 | Brunner et al. ............. 382/128 |
| 2008/0064949 A1* | 3/2008 | Hertel et al. ................ 600/407 |
| 2008/0273784 A1* | 11/2008 | Pfister ........................ 382/131 |

OTHER PUBLICATIONS

Toshiya Takahashi, et al., "Internet Video Distribution Using Image-Separated Multi-Layer Video Compression Technology", Eizojoho Industrial, vol. 32, No. 9, May 1, 2000. pp. 31-35 with partial English translation.

Toshihiko Wakahara, et al., "Configuration and Characteristics of Distance Learning System over ATM-PVC Network", The Transactions of the Institute of Electronics, Information and Communication Engineers, vol. J81-B-I, No. 8, Aug. 25, 1998, pp. 494-506 with partial English translation.

Mamoru Harada, et al., "Network Load Reduction in TV Broadcast by Distribution with Relay Servers", Nikkei Electronics, No. 653, Jan. 15, 1996, pp. 76-82 with partial English translation.

* cited by examiner

FIG.5A

| LAYER ID | IN-LAYER ELEMENT ID | LOCATION | SCENE | ... | TRANSMISSION DESTINATION HISTORY | TRANSMISSION MEANS |
|---|---|---|---|---|---|---|
| XXXYY773 | BUTTON 1 | 30,45 | ALL | | XXYYZZWW | Protocol 1 |
| | BUTTON 2 | 45,45 | | | XXYYZZPPP | Protocol 1 |
| | BUTTON 3 | 45,30 | | | XXYYZZUUU | Protocol 1 |
| | ... | ... | | | ... | ... |

FIG.5B

| LAYER ID | IN-LAYER ELEMENT ID | LOCATION | SCENE | ... | TRANSMISSION DESTINATION HISTORY | TRANSMISSION MEANS |
|---|---|---|---|---|---|---|
| XXXYY823 | UNDERLAY 1 | 200,5 | STILL IMAGE | | XXYYZZWW | Protocol 1 |
| | UNDERLAY 2 | 700,5 | | | XXYYZZPPP | Protocol 1 |
| | UNDERLAY 3 | 200,505 | | | XXYYZZPPP | Protocol 2 |
| | ... | ... | | | ... | ... |

FIG.5C

| LAYER ID | IN-LAYER ELEMENT ID | LOCATION | SCENE | ... | TRANSMISSION DESTINATION HISTORY | TRANSMISSION MEANS |
|---|---|---|---|---|---|---|
| XXXYY832 | UNDERLAY 1 | 200,5 | MOVING IMAGE | | XXYYZZWW | Protocol 1 |
| | UNDERLAY 2 | 700,5 | | | XXYYZZPPP | Protocol 1 |
| | UNDERLAY 3 | 200,505 | | | XXYYZZPPP | Protocol 3 |
| | ... | ... | | | ... | ... |

FIG.5D

| LAYER ID | IN-LAYER ELEMENT ID | LOCATION | SCENE | ... | TRANSMISSION DESTINATION HISTORY | TRANSMISSION MEANS |
|---|---|---|---|---|---|---|
| XXXYY772 | OVERLAY (ANNEX CHARACTERS) | 200,5 | ALL | | XXYYZZWW | Protocol (S) |
| | OVERLAY (ANNEX CHARACTERS) | 700,5 | | | XXYYZZPPP | Protocol (S) |
| | OVERLAY (ANNEX CHARACTERS) | 200,505 | | | XXYYZZUUU | Protocol 1 |
| | ... | ... | | | ... | ... |

FIG.5E

| LAYER ID | IN-LAYER ELEMENT ID | LOCATION | SCENE | ... | TRANSMISSION DESTINATION HISTORY | TRANSMISSION MEANS |
|---|---|---|---|---|---|---|
| XXXYY773 | OVERLAY(ROI)1 | 200,5 | ALL | | XXYYZZWW | Protocol 1 |
| | OVERLAY(ROI)2 | 700,5 | | | XXYYZZPPP | Protocol 1 |
| | OVERLAY(ROI)3 | 200,505 | | | XXYYZZPPP | Protocol 1 |
| | ... | ... | | | ... | ... |

MEDICAL IMAGE DISPLAY SYSTEM AND MEDICAL IMAGE COMMUNICATION METHOD

CROSS-REFERENCE TO RELATED APPLICATION

This application is based upon and claims the benefit of priority from the prior Japanese Patent Application No. 2009-166892, filed on Jul. 15, 2009, and Japanese Patent Application No. 2010-151085, filed on Jul. 1, 2010, the entire contents of which are incorporated herein by reference.

FIELD

Embodiments described herein relate to a medical image display system and a medical image communication method for delivering medical image display data and a display/clinical application to a client terminal by way of a network.

BACKGROUND

There are known client/server systems for connecting an application server and a client terminal by way of a network to allow the client to log in at the server machine from an application for connection of the client terminal in order to display and operate an application held by the server. In such a system, medical display information and information for user operations are transmitted to the client terminal by means of a same network protocol.

For example, a mouse click or a keyboard operation at the client terminal is hooked by the application for connection and the operation event is transmitted to the server. The server executes a process (e.g., of calling an image or inputting character information) that corresponds to the received operation event and the medical display information is transmitted from the server to the application for connection on the client terminal by way of the network. The medical display information is rendered into an image, which is then displayed and updated on the terminal by utilizing the display resource of the client terminal.

In a client/server system as described above, if it is held in a LAN environment where bands exceeding 100 M-bit/second exist, the network bands are occupied to a large extent as a result of displaying and updating large volume images as moving images are reproduced and/or three-dimensional CAD software for editing/viewing a three-dimensional image from various angles is utilized so that consequently the processing speed does not catch up the volume of data to be processed. Then, there arises a problem that the user operation instruction from the terminal delays to give rise to a degraded user response. Additionally, if a single communication protocol for display is employed in a network environment from the server down to the terminal, there also arise problems including that the secure communication encoding/decoding cost becomes high and that the performance is damaged for patient information.

BRIEF DESCRIPTION OF THE DRAWINGS

FIGS. 5A through 5E are illustrations of exemplary layer formation tables; and

DETAILED DESCRIPTION

Figure 1:
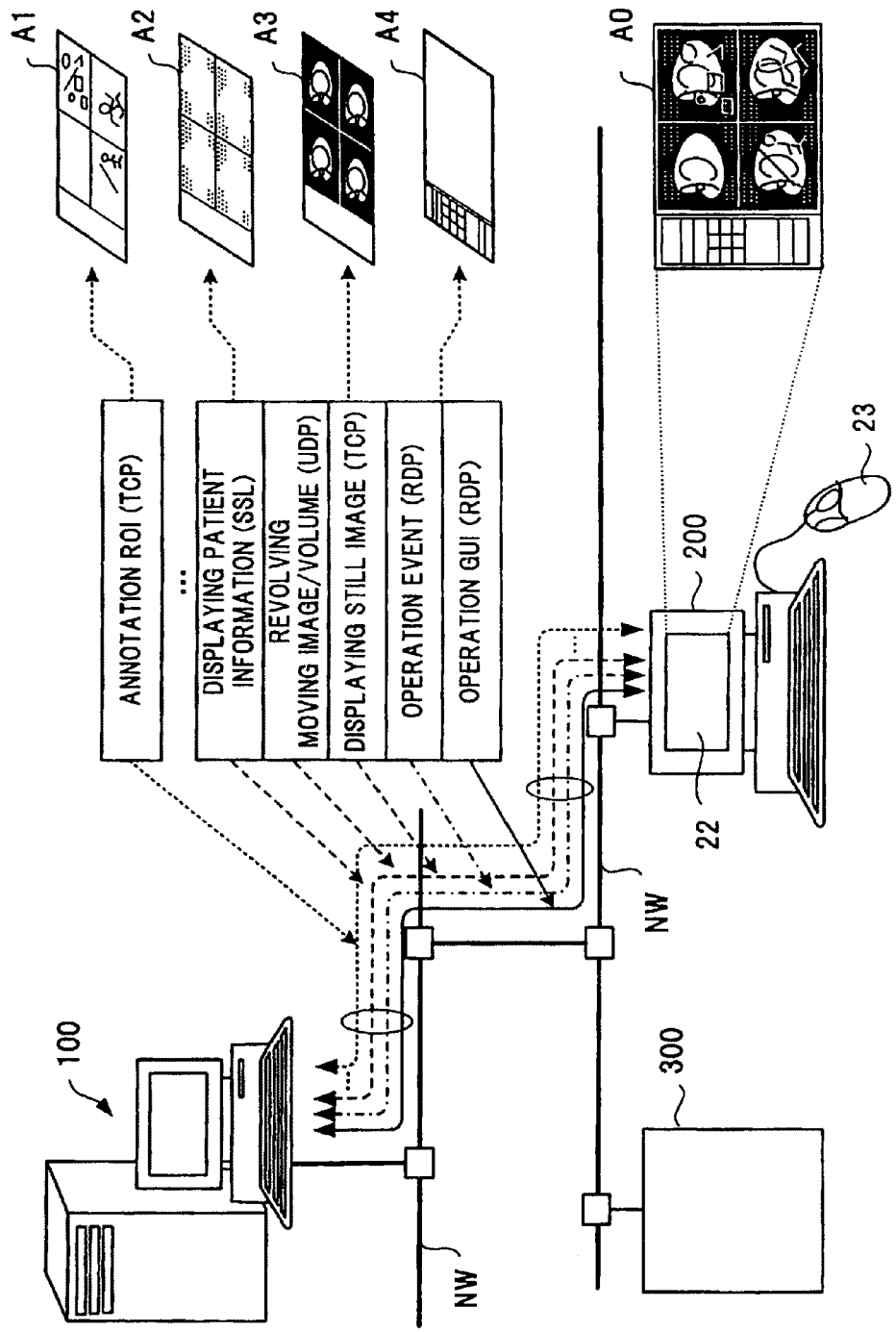
FIG. 1 is a schematic illustration of a medical image display system according to an embodiment, showing the overall configuration thereof.

A medical image display system according to an embodiment including a server that provides medical image display data and display/clinical applications and a terminal device that can access the server by way of a network, said system comprising, configuring the medical image display data so that pieces of image display information of a plurality of types including medical image information and interface information for user operation are arranged in a multilayered manner; transmitting the pieces of image display information of a plurality of types to the terminal device from the server, assigning them to communication protocols of different types; synthetically combining and displaying the pieces of image display information of a plurality of types transmitted from the server with use of the terminal device; and generating operator information by utilizing the interface information for user operation displayed on the terminal device, and transmitting the operator information to the server by way of the network.

The embodiment of medical image display system will be described in detail by referring to the drawings. Note that, throughout the drawings, same parts are designated by same reference symbols.

FIG. 1 is a schematic illustration of an embodiment of medical image display system, showing the configuration thereof. The system of FIG. 1 includes an application server 100 connected to a network and a plurality of client terminals 200, 300, . . . . The application server 100 provides medical image display data and display/clinical application for the data to the terminals 200, 300, . . . . The client terminal 200 has an image display means (monitor) 22 and an image operation means 23 such as a mouse.

The client terminals 200, 300, . . . can acquire medical image display data from the application server 100 by accessing the application server 100 and display medical information on the monitor 22. The medical image display data are data for displaying medical information and typically include pieces of image display information of a plurality of types such as examination data, image data, a doctor's comment, annex information and interface information for user operations as well as information for determining display arrangements and display positions. Interface information for user operations is operation GUI (graphical user interface) information.

Pieces of image display information of such a plurality of types are synthetically combined in a multilayered manner as image layers laid one on the other and displayed on the client terminals 200, 300 . . . . Control information (operator information) generated by the terminal user can be transmitted to the application server 100 by a user operation to update the pieces of image display information and perform other operations as the operation GUI that is displayed on the client terminal 200, 300, . . . is operated.

While a plurality of client terminals 200, 300, . . . are connected to the application server 100, communication processes that are executed between the application server 100 and the client terminal 200 will be described below. The application server 100 and the client terminal 200 may also be referred to simply as server and terminal respectively in the following description.

As shown in FIG. 1, the application server 100 and the client terminal 200 are connected by a network NW. In this embodiment, pieces of image display information of a plurality of different types are assigned to respective communication protocols for communication and control information (operator information) generated by a user operation is transmitted to the server 100 by way of a transmission band ensured on the network NW.

When, for example, the operator cancels a moving image that is being reproduced at the terminal 200, a control instruction for delivery suspension of the moving image information can be transmitted to the application server 100 without delay by way of an information transmission protocol of control instruction because a transmission band is ensured for operator information so that the server 100 can immediately suspend the delivery.

Display regions are assigned to the pieces of medical information (A0) that are to be displayed on the terminal 200 according to the types of image display information and pieces of image display information of a plurality of types are transmitted from the server 100 by means of respective communication protocols. For example, moving image information is transmitted between the server 100 and the terminal 200 by means of a light load communication protocol such as UDP (user datagram protocol) to minimize the load of the transmission band for transmitting a large volume moving image information. Annotation ROI (A1) and still image information (A3) may, for example, be transmitted by means of a different communication protocol such as TCP (transmission control protocol).

The UDP is a connectionless type communication protocol for transmission without any acknowledgement of arrival of transmitted data to a communication partner that can raise the communication speed. On the other hand, TCP is a connection type communication protocol for transmission with an acknowledgement of arrival of data to a communication partner. The communication partner returns the received data accompanied by ACK (acknowledgment) for acknowledging the arrival of the data. A connection type communication protocol ensures reliable communications but provides only a low communication speed.

The annex information (A2) including patient information is transmitted by means of a communication protocol such as SSL (security sockets layer) protocol that guarantees security. The annex information is transmitted typically in the form of text information and information specifying the position and the font size for displaying the text is included in the annex information. Alternatively, the annex information may be bit-mapped for transmission. Operation events and operation GUI (A4) are transmitted by means of a terminal communication protocol such as RDP (remote desktop protocol). Thus, the bandwidth and the encoding/decoding cost are minimized but the security of communication is improved.

Figure 2:
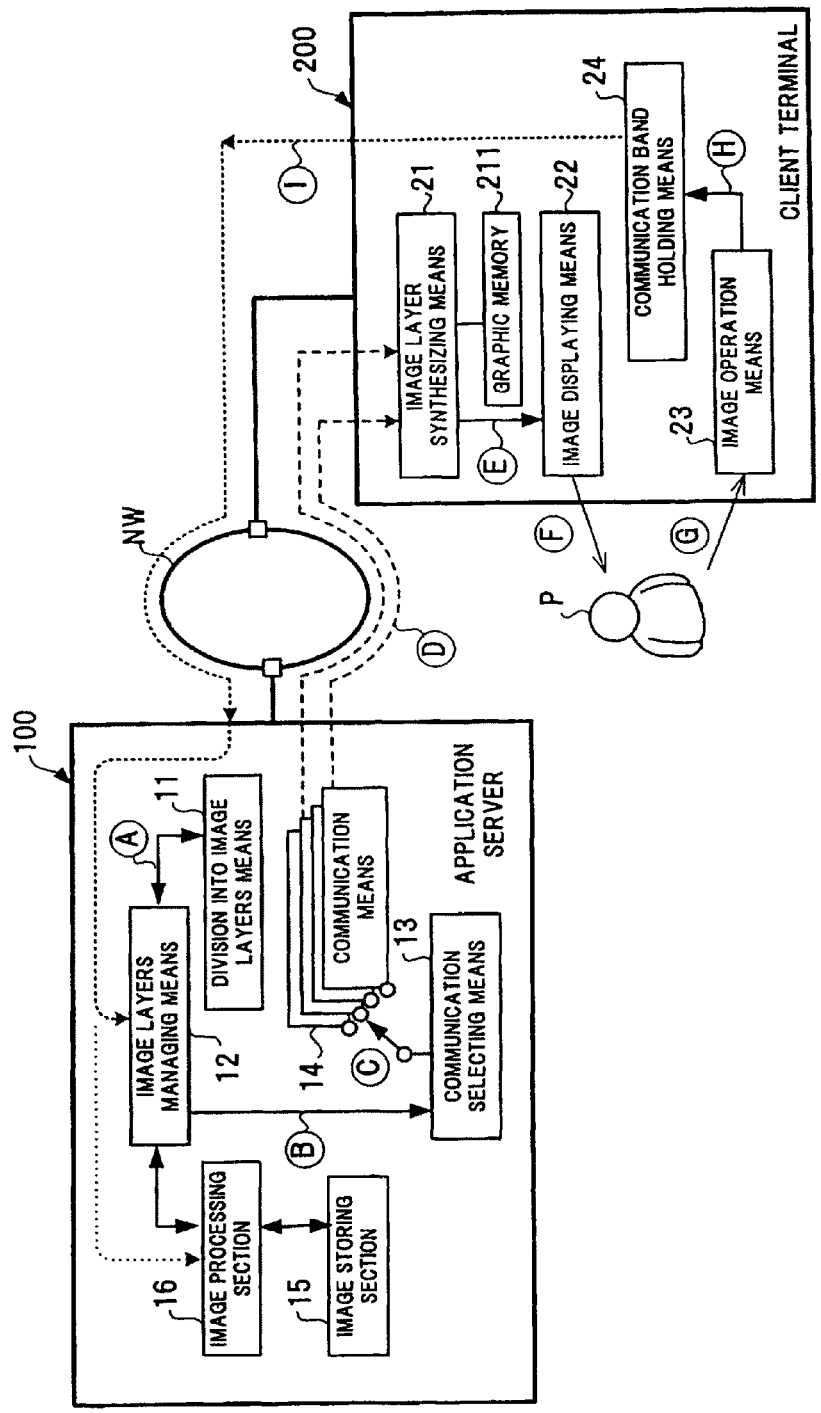
FIG. 2 is a schematic block diagram, showing the configuration of the server and that of the client terminal.

FIG. 2 is a schematic block diagram, showing the configuration of the application server 100 and that of the client terminal 200.

Referring to FIG. 2, the application server 100 has a division into image layers means 11, an image layers managing means 12, a communication selecting means 13, a plurality of communication means 14, an image storing section 15 and an image processing section 16. On the other hand, the client terminal 200 has an image layer synthesizing means 21, an image displaying means 22, an image operation means 23 and a communication band holding means 24.

The application server 100 provides medical image display data and a display/clinical application for them to the client terminal 200 that is connected to the network NW and the data flow at the terminal 200 after the client terminal 200 logs in at the application server 100 follows the sequence shown below.

Figure 3:
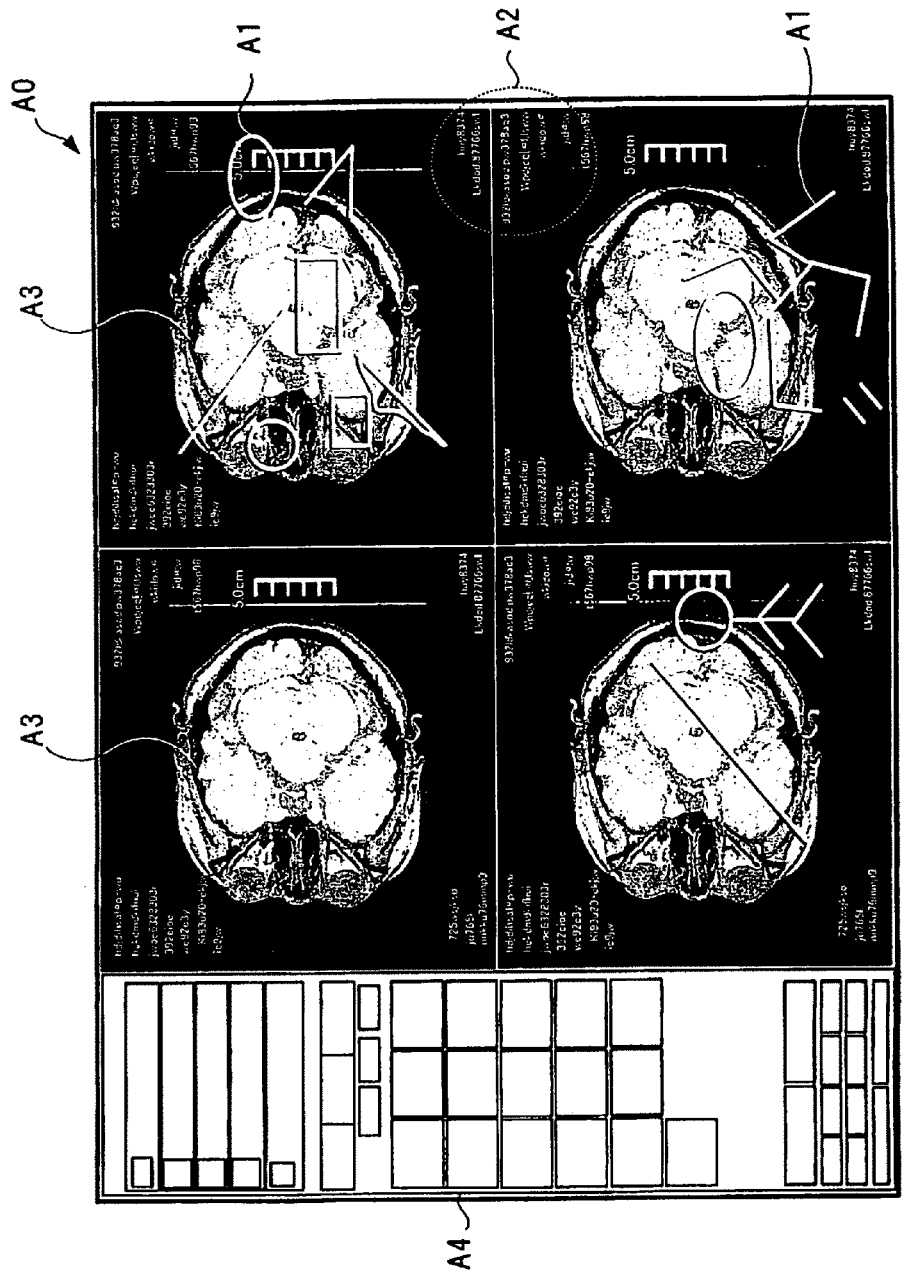
FIG. 3 is an illustration of an exemplary displayed image at a client terminal.

Firstly, the medical image display data provided onto the client terminal 200 by the application server 100 are processed and displayed on the image displaying means 22. FIG. 3 is an illustration of an exemplary image of the medical information A0 displayed at the terminal 200, where operation GUI information (A4), examination images (A3) including still images and moving images (four images in this example), annex information (A2) including patient information and annotation ROI (A1) including the comments written by the operator (doctor) are synthetically combined in a multilayered manner.

Figure 4:
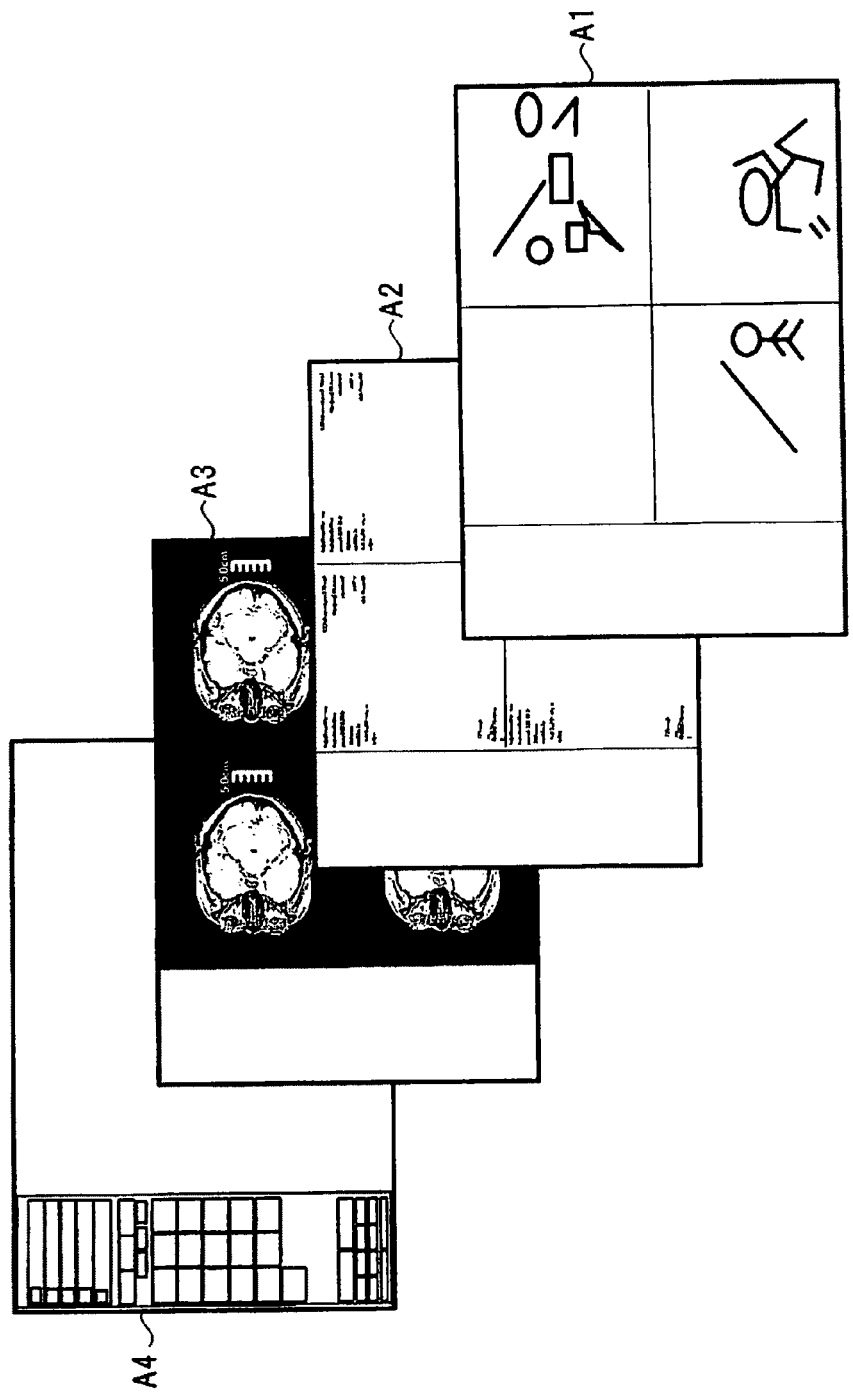
FIG. 4 is an illustration, showing the formation of the layers of a displayed image.

Of these pieces of image information, for example, the operation GUI information A4 is placed at the lowermost layer and the examination images A3 including still images and moving images are placed thereon while the patient information A2 and the annotation information A1 are placed at upper layers as shown in FIG. 4.

Medical information A0 as shown in FIG. 3 is prepared by processing the image information stored in the image storing section 15 by the image processing section 16. More specifically, the image processing section 16 prepares image layers that are synthesized in a multilayered manner according to the directive of the image layer managing means 12. As shown in FIG. 2, medical information A0 is displayed by way of a process flow including stages of (A) division into image layers, (B) provision of image layers updating information, (C) selection of image layers communication means, (D) transmission of image layers display information, (E) synthesis of image layer and so on.

Before describing the elements A through E of the process flow, an image layer will be described below. Medical image display data and the display/clinical application thereof are formed by a plurality of image elements.

Referring to the display example of FIG. 3, the screen of the client terminal 200 is formed by elements having image position information and overlap information in the image depth direction on the display region A4 for displaying operation GUI information (buttons, etc.) for the user interface, the display region A3 for the examination image including still images and moving images, the annex information display region A2 for patient information and other information, the annotation ROI display region A1 that is a region for rendering to medical images and so on.

An image layer refers to image elements constituting medical image display data and the display/clinical application thereof. An image layer is formed by arranging 1 through n (a plurality of) image elements such as image elements A4 through A1 shown in FIG. 4. The medical information (A0) is formed by overlapping 1 through n image layers. FIG. 3 shows an image formed by a plurality of overlapping image layers shown in FIG. 4.

Note that four examination image display regions are combined as a set and a medical image A0 formed by synthetically combining the four examination image display regions and annex information and annotation ROI annexed to the four examination image display regions in a multilayered manner is shown in FIGS. 3 and 4. However, a medical image A0 may alternatively be formed by synthetically combining a single examination image display region and information annexed to it. Still alternatively, a medical image A0 may be formed by synthetically combining a plurality of examination image display regions other than four that are in a divided state.

The stages A through E of process flow will be described below, following the flow of information, by referring to FIG. 2.

(A) division into image layers: The image layers managing means 12 divides the display screen (see FIG. 3) according to the network traffic and the layer formation history at the time of the last connection grasped as the terminal 200 logs in into 1 through n (a plurality of) image layers, using the division into image layers means 11. The formation of image layers is defined by a plurality of layer initial formation templates arranged according to the network transfer band at the time of initial connection from the terminal 200 to the server 100. A layer initial formation template refers to image formation of defining the position of an operation region, the number of images (e.g., four) and so on.

(B) provision of image layers updating information: The division into image layers means 11 provides the raster data themselves on the time-divided graphic memory, the raster data as moving image and image revolving scene information, the annex information as character information and so on to the communication selecting means 13 by way of the image layers managing means 12.

(C) selection of image layers communication means: The layer information after the division is allocated to any of a plurality of communication means 14 by the communication selecting means 13. The communication means 14 are equipped with a plurality of communication protocols in advance and an image layer having a high transmission rate is tuned up so as to use a light load communication protocol. Assignment of an image layer that is to be hidden on the transmission route such as the patient name is defined in a layer formation table so as to use an encrypted path. Layer formation tables are described hereinafter by referring to FIGS. 5A through 5E.

The communication selecting means 13 monitors the communication load situation of the network NW and the quantity of data that each image layer uses and, if information using a large quantity of data is to be transmitted, the communication selecting means 13 selects a communication means 14 of a protocol that puts a light load on the network. A method of transmitting information by way of the network, feeding it back and measuring the delay time of the fed back information may be used as a method for monitoring the communication load situation of the network NW.

(D) transmission of image layers display information: The communication means 14 are equipped with a plurality of different communication protocols and selects one of the communication protocols (communication means 14) by the communication means selecting means 13 to communicate with the terminal 200. The communication means 14 is basically transmission protocols between networks NW that include, for example, RDP, X11 (Unix type Rsh) protocol, TCP/IP protocol for a plurality of sessions, UDP/IP protocol for a plurality of sessions and SSL protocol and ensures a plurality of network routings getting to the terminal 200 if the communication means 14 can do so.

The client server system for providing medical image display data and the display/clinical application thereof to the network terminal 200 may be formed, for example, in such a way that an operator P operates the display/clinical application, using the image displaying means 22 and the image operation means 23 connected to the application server 100 itself. If such is a case, the fastest transmission means on the data transmission architecture in the application server 100 is employed although the protocol is said to transmit the network NW.

FIGS. 5A through 5E are illustrations of exemplary layer formation tables. Formation tables as shown in FIGS. 5A through 5E can be prepared by turning the definitions of image layer formations into data. An image layer formation table includes items such as layer ID, in-layer element ID, location, scene, transmission destination history, transmission means and so on.

FIG. 5A is a layer formation table relating to the operation GUI (A4) of a lower layer. In FIG. 5A, layer ID shows the type of image layer and in-layer element ID shows the elements (such as buttons) while location shows the display region and scene shows if all or part. Transmission destination history shows history telling which communication protocol is used to transmit information to which terminal by referring to the IP address and transmission means shows the type of communication protocol. More often than not, a standard communication means that is optimized by the operating system such as RDP or X11, Rsh is selected as the transmission means of the operation GUI when that the operation GUI is closely linked to the operating system is taken into consideration.

FIG. 5B, FIG. 5C, FIG. 5D and FIG. 5E are layer formation tables relating respectively to a still image A3, a moving image A3, annex information A2 and annotation ROI information A1.

Availability or unavailability of the protocol is determined at the time of logging in from the terminal, at the time of forming an image layer and at the time of altering the transmission protocol and, if the protocol is unavailable, the layer formation tables of FIGS. 5A through 5E are updated according to the information on the unavailability. Additionally, at the time of logging in from the terminal, at the time of forming an image layer or at the time of altering the transmission protocol, the image layers formed by the session during the logging in are shared by the application server 100 and the terminal 200 as the image layer formation tables are transmitted appropriately from the application server 100 to the image layer synthesizing means 21 of the target terminal.

(E) synthesis of image layer: The raster data transmitted to the terminal 200 as moving image or image revolving scene information by the selected communication protocol and the annex information that is also transmitted are received by the image layer synthesizing means 21 of the client terminal 200 and unfolded on the graphic memory 211 of the client terminal 200 as time series buffer.

When the image displaying means 22 is updating the display at a certain frame rate, a buffer is prepared in the graphic memory 211 for the next display. If the memory buffer for the next display should be updated or not is determined on the basis of the received protocol and the clock time of the reception. If the used protocol is TCP and the graphic memory buffer has been updated for the related area, for example, the received data are held and hence assigned to the after the next graphic memory buffer.

If the used protocol is UDP (user datagram protocol) and the graphic memory buffer has been updated for the related area, the graphic memory buffer for the next display is overwritten by the received data. The transmission timing is recorded in TCP and the inherited protocol thereof and the image layers that are produced by division through a plurality of sessions are unfolded on the graphic memory buffer using the timing as key.

By any of the above-described updating methods, a rendering region that is highly frequently updated can be displayed efficiently, while suppressing the consumption of the network bands. Additionally, the security of the entire transmission system can be ensured efficiently by assigning encrypted communication paths to part of the image layers (layers that needs to be hidden) to be transmitted.

Next, transfer of the operator information prepared by the operator P will be described below. The operator information prepared by the operator P is transferred to the application server 100 by way of a process flow including stages of (F) transfer of display information, (G) transfer of operation event, (H) transmission of operation event and (I) transfer of operator information. Stages (F) through (I) of the process flow will be described below by referring to FIG. 2.

(F) transfer of display information: The operator P observes the screen on the client terminal 200. The screen of the client terminal 200 is employed, for example, for analysis of the brain blood flow and analysis of a heart disease. The operator P also observes the numerical data obtained from the blood flow value of the brain blood flow and so on for diagnosis.

(G) transfer of operation event: The operator P operates the application and the image from the client terminal 200, exclusively using the image operation means 23 on the client terminal 200. In a typical example, the operator P may dynamically alter ww/wl of the image or revolve the 3D image that is being displayed to alter the viewing direction by depressing the application operation GUI (the leftmost button in FIG. 3) arranged on the image displaying means 22 of the client terminal 200 and/or mouse-dragging the image (underlayer image A3 in FIG. 3) on the image displaying means 22 of the client terminal 200. Or, the operator P may enlarge or reduce part of the image, adjust the color mapping, turn images at high-speed and/or display images that are laid one on the other at a same position (fusion).

(H) transmission of operation event: The operation information of the operator P from the image operation means 23 is converted into an operation event that software can translate from the electric signal produced from a physical device. For example, the event name that indicates a mouse click to which coordinate information is added to indicate the click position may be transmitted to the operator information communication band holding means 24 as mouse click event.

(I) transfer of operator information: Operation events are stored in the operation information communication band holding means 24 on a time series basis and transmitted to the application server 100 at regular time intervals by way of the network NW, which are correlated to the rendering/updating frame rate. In other words, when operation events are to be transmitted from the client terminal 200 to the application server 100, a band for transmission is ensured in advance typically on a time division communication basis so that they may be transmitted smoothly.

The purpose of transmission of operation events is to transmit operation information quickly to the application server 100 in a network bands shortage situation that arises because of a heavy load situation of the terminal 200 or some other reason by minimizing the influence of the shortage situation.

Therefore, when the operator P logs in, an operation event transmission band is ensured in advance. For example, a route different from the image layer display line may be routed by network routing. Alternatively, an environment where operation events can be transferred without delay may be provided by polling communication that is conducted at regular time intervals. Still alternatively, when the terminal 200 has a heavy load, it is detected and the stored operation events are transmitted to the application server 100 at time intervals that are smaller than the normal operation event transmission frequency.

To make such operations possible, the software module and the hardware module that bear the image operation means 23 and the operation information communication band holding means 24 need to operate with high priority relative to the means that bears the image display.

On the other hand, the operation events that are transmitted by way of the network NW are received by the image layers managing means 12 of the application server 100 and image layers are prepared by the image processing section 16 according to a directive of the image layers managing means 12. Alternatively, the image processing section 16 may directly receive the operation events and prepare image layers.

The operation events received by the application server 100 are notified to the software module where medical image display data and display/clinical applications that operate on the application server 100 are arranged in the form of an interrupt event. The software module update the raster data themselves on the graphic memory 211 of the division into image layers means 11 and the annex information such as raster data difference information of moving image and image revolving scene information and annex information of character information in accordance with the operation events. Thereafter, the image update that corresponds to the operation information of the operator P is completed as the stages A through E and the stages F through I of the process flow are followed.

Figure 6:
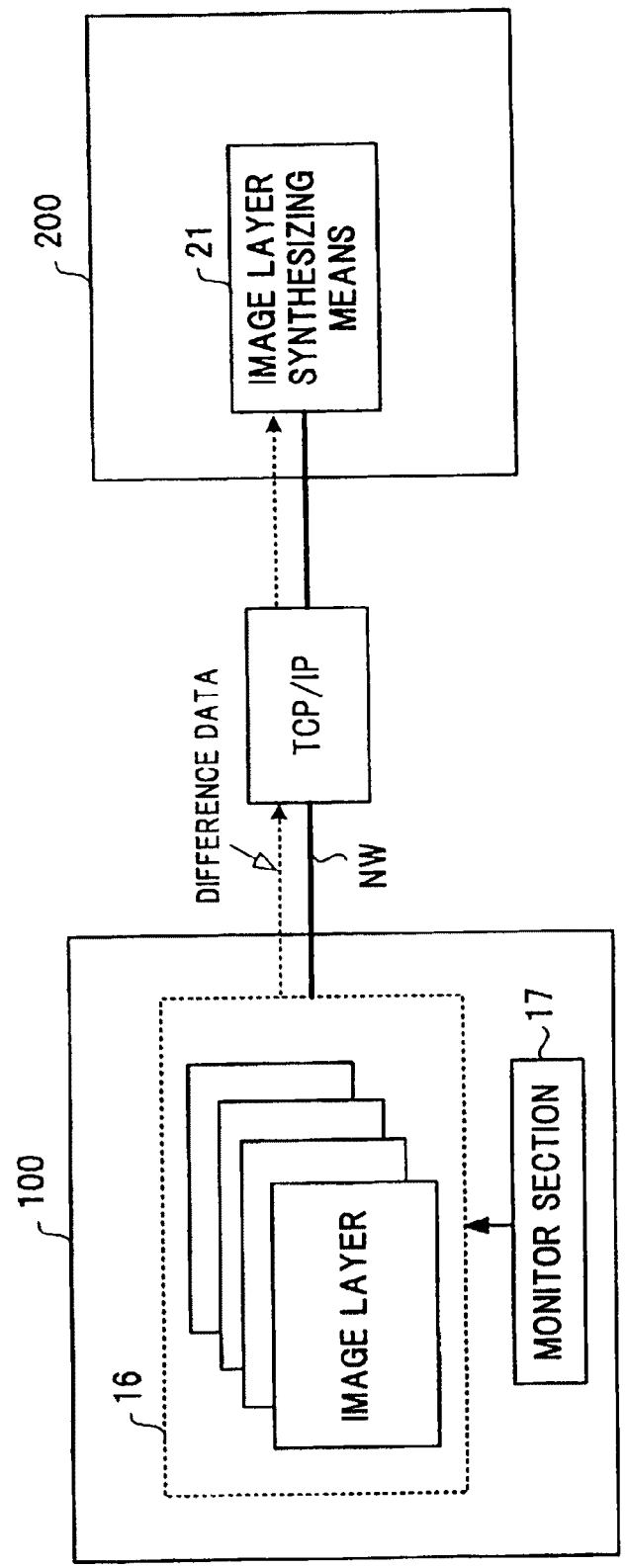
FIG. 6 is a schematic block diagram, showing an example of data transmission between a server and a client terminal.

FIG. 6 is a schematic block diagram, showing an example of data transmission between the server 100 and the client terminal 200. FIG. 6 shows the transmission format when the medical image display data prepared by the server 100 is partly altered. A monitor section 17 is provided in the server 100 and monitors if there are data that are altered for any of the plurality of image layers prepared by the image processing section 16 or not. If the monitor section 17 determines that there are data for any of the image layers that is or are altered, the server 100 transmits difference data of the difference from the data that have already been transmitted (data on the altered image layer (s)) to the client terminal 200 by way of the network NW. FIG. 6 shows an instance where difference data are transmitted by using TCP/IP protocol.

The client terminal 200 updates the image layers according to the transmitted difference data and displays them. Therefore, if the medical image display data are partly altered, it is not necessary to transmit all the medical image display data once again. In other words, it is sufficient to transmit only the difference data to realize an efficient data transmission.

With the above-described embodiment, the user response can be improved and the security of transmitted information can be ensured by using different transmission protocols for image display information and operator information and assigning an optimum transmission protocol to each image layer for transmission between the server and the terminal.

Further, not limited to the above described-embodiment, and can be variously modified. For example, the communication protocol that is employed for the communication means 14 may be other than the exemplary protocols described in the text.

While a certain embodiment has been described, the embodiment has been presented by way of example only, and is not intended to limit the scope of the invention. Indeed, the novel methods and systems described herein may be embodied in a variety of other forms; furthermore, various omissions, substitutions and changes in the form of the methods and systems described herein may be made without departing from the spirit of the inventions. The accompanying claims and their equivalents are intended to cover such forms or modifications as would fall within the scope and spirit of the inventions.

What is claim is:

1. A medical image display system, comprising:
a server that provides medical image display data and display/clinical applications; and
a terminal device that can access the server by way of a network, wherein the server is configured to:
   process the medical image display data so that pieces of image display information of a plurality of types, comprising medical image information, which includes annotation information, annex information, still image information, and moving image information, and interface information for user operation, are arranged synthetically combined in a multilayered manner as image layers;
   divide the multilayered medical image display data into the pieces of the image display information of the plurality of types for display on the terminal device, and manage the divided image display information; and
   transmit the pieces of image display information of the plurality of types to the terminal device from the server, assigning a communication protocol of a plurality of communication protocols of different types to each of the image layers, the communication protocols including a first type free of an acknowledgement of arrival of transmitted data to a communication partner, and a second type that includes the acknowledgement of the arrival of the transmitted data to the communication partner; and
the terminal device is configured to:
   synthetically combine, in a multilayered manner as the image layers, and display the pieces of image display information of the plurality of types transmitted from the server; and
   generate operator information by utilizing the interface information for user operation displayed on the terminal device, and transmit the operator information to the server by way of the network; and
wherein the server comprises:
   a division section configured to divide the medical image display data at least into the annotation information, the still image information, the moving image information, and the annex information, which includes patient information; and
   a communication section configured to transmit at least the annex information by an SSL (Secure Sockets Layer) protocol.

2. The system of claim 1, wherein the server comprises a selection section configured to select the pieces of the image display information of the plurality of types, wherein the communication section is configured to transmit the pieces of the image display information of the plurality of types selected by the selection section to the terminal device by the plurality of communication protocols of different types.

3. The system of claim 2, wherein
the selection section is configured to select the plurality of communication protocols according a communication load situation of the network and a volume of used data of the divided pieces of the image display information of the plurality of types so as to transmit the pieces of the image display information that use a large volume of data by a communication protocol for a light network load.

4. The system of claim 3, wherein
the communication section is configured to transmit the pieces of the image display information that use a large volume of data by a connectionless-type communication protocol free of an acknowledgement of arrival of transmitted data to a communication partner, and transmit the pieces of the image display information that use a small volume of data by a connection-type communication protocol that includes the acknowledgement of the arrival of the transmitted data to the communication partner.

5. The system according to claim 2, wherein
the terminal device comprises a display section configured to synthetically combine and display the medical information transmitted by the communication section and the interface information for user operation, and an operation section configured to operate the displayed interface information for user operation.

6. The system of claim 1, wherein
the operator information is transmitted to the server by way of a transmission band ensured on the network.

7. The system of claim 1, wherein,
the server is configured to transmit to the terminal device difference information from the image display information that has already been transmitted, when the pieces of the image display information of the plurality of types are partly altered, and
the terminal device is configured to update the image display information according to the difference information, and display the updated image display information.

8. A medical image communication method, comprising:
processing medical image display data so that pieces of image display information of a plurality of types, comprising medical information, which includes annotation information, annex information, still image information, and moving image information, and interface information for user operation, are arranged synthetically combined in a multilayered manner as image layers;
dividing the multilayered medical image display data into pieces of the image display information of the plurality of types for display on a terminal device, and managing the divided image display information;
transmitting the pieces of the image display information of the plurality of types to the terminal device from a server, assigning a communication protocol of a plurality of communication protocols of different types to each of the image layers, the communication protocols including a first type free of an acknowledgement of arrival of transmitted data to a communication partner, and a second type that includes the acknowledgement of the arrival of the transmitted data to the communication partner;
synthetically combining, in a multilayered manner as the image layers, and displaying the pieces of image display information of the plurality of types transmitted from the server; and
generating operator information by utilizing the interface information for user operation displayed on the terminal device, and transmitting the operator information to the server by way of a network; and
wherein the method further comprises:
   dividing the medical image display data at least into the annotation information, the still image information, the moving image information, and the annex information, which includes patient information; and
   transmitting at least the annex information by an SSL (Secure Sockets Layer) protocol.

9. The method of claim 8, further comprising: selecting respectively the pieces of the image display information of the plurality of types, and transmitting the pieces of the image display information of the plurality of types selected, respectively, to the terminal device by the plurality of communication protocols.

10. The method of claim 9, further comprising:
selecting the plurality of communication protocols according to a communication load situation of the network and a volume of used data of the divided pieces of the image display information of the plurality of types so as to transmit the pieces of the image display information that use a large volume of data by a communication protocol for a light network load.

11. The method of claim 10, further comprising:
transmitting the pieces of the image display information that use the large volume of data by a connectionless-type communication protocol free of an acknowledgement of arrival of transmitted data to a communication partner, and transmitting the pieces of the image display information that use a small volume of data by a connection-type communication protocol that includes the acknowledgement of the arrival of the transmitted data to the communication partner.

12. The method of claim 8, wherein the combining and displaying step comprises:
synthetically combining and displaying the medical information and the interface information for user operation and operating the displayed interface information for user operation.

13. The method of claim 8, further comprising:
transmitting the operator information to the server by way of a transmission band ensured on the network.

14. The method of claim 8, further comprising:
transmitting to the terminal device, difference information from the image display information that has already been transmitted, when the pieces of the image display information of the plurality of types are partly altered, and
updating the image display information according to the difference information, and displaying the updated image display information.

* * * * *